United States Patent
Sato et al.

(10) Patent No.: US 8,055,320 B2
(45) Date of Patent: Nov. 8, 2011

(54) VITAL INFORMATION MEASURING DEVICE

(75) Inventors: Makoto Sato, Sakai (JP); Yoshiroh Nagai, Nishinomiya (JP); Kazumi Kitajima, Higashiosaka (JP)

(73) Assignee: Konica Minolta Sensing, Inc., Sakai-shi (JP)

(*) Notice: Subject to any disclaimer, the term of this patent is extended or adjusted under 35 U.S.C. 154(b) by 1409 days.

(21) Appl. No.: 11/589,649

(22) Filed: Oct. 30, 2006

(65) Prior Publication Data

US 2007/0100221 A1    May 3, 2007

(30) Foreign Application Priority Data

Oct. 31, 2005 (JP) .................................. 2005-317241

(51) Int. Cl.
    *A61B 5/1455* (2006.01)
(52) U.S. Cl. ........................................ 600/323; 600/310
(58) Field of Classification Search ........... 600/300–500
    See application file for complete search history.

(56) References Cited

U.S. PATENT DOCUMENTS

| | | | |
|---|---|---|---|
| 4,898,180 A * | 2/1990 | Farrelly et al. ................. | 600/494 |
| 4,955,379 A | 9/1990 | Hall ................................ | 128/633 |
| 4,982,738 A | 1/1991 | Griebel .......................... | 128/670 |
| 5,197,489 A * | 3/1993 | Conlan ........................... | 600/595 |
| 5,675,553 A * | 10/1997 | O'Brien et al. ................. | 367/135 |
| 6,292,692 B1 * | 9/2001 | Skelton et al. .................. | 607/5 |
| 6,356,520 B1 * | 3/2002 | Hanamoto et al. ............. | 369/47.1 |
| 2005/0222502 A1 * | 10/2005 | Cooper .......................... | 600/323 |

FOREIGN PATENT DOCUMENTS

| | | |
|---|---|---|
| JP | 1-153139 A | 6/1989 |
| JP | 02-305552 A | 12/1990 |
| JP | 05-197439 A | 8/1993 |
| JP | 2000-312669 A | 11/2000 |
| JP | 2001-190503 A | 7/2001 |

OTHER PUBLICATIONS

Japanese Notice of Reasons for Rejection dated Jun. 29, 2010, for counterpart Japanese Application No. 2006-264778, together with an English translation thereof.

* cited by examiner

*Primary Examiner* — Eric Winakur
*Assistant Examiner* — Marjan Fardanesh
(74) *Attorney, Agent, or Firm* — Sidley Austin LLP

(57) ABSTRACT

A vital information measuring device includes: a measuring unit for measuring certain vital information concerning a living body; a storage for storing therein a signal outputted from the measuring unit as measurement data; a vital information acquirer for acquiring a sleep apnea index based on the measurement data stored in the storage; a display section for displaying the sleep apnea index acquired by the vital information acquirer; and a device body for integrally mounting the measuring unit, the storage, the vital information acquirer, and the display section.

14 Claims, 12 Drawing Sheets

FIG.1
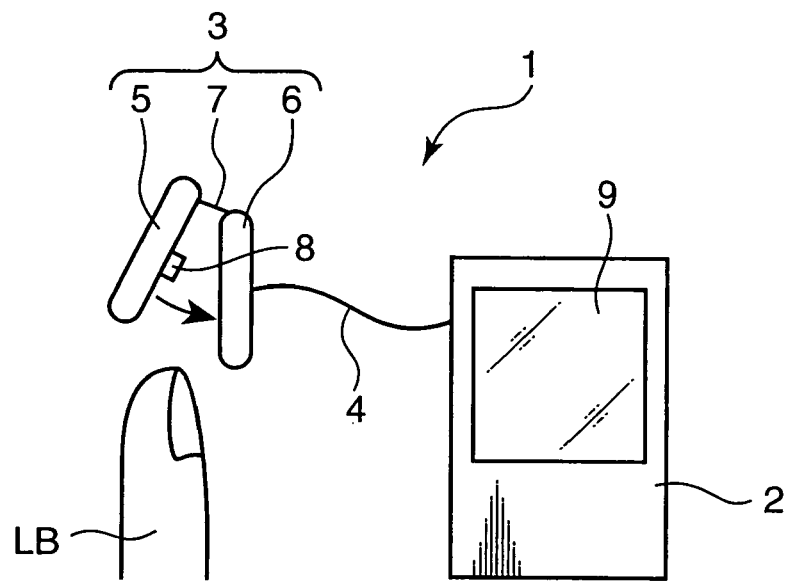
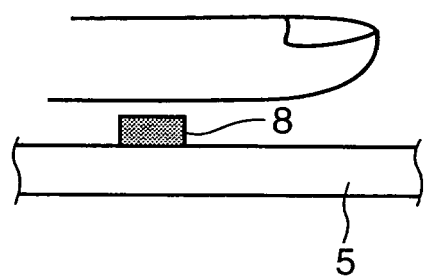
FIG.2A
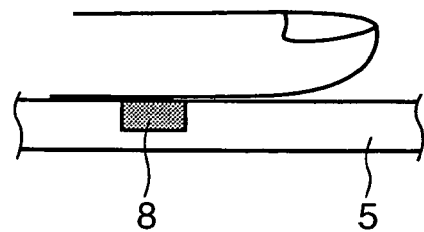
FIG.2B

PHOTOELECTRIC PULSE WAVE SIGNAL

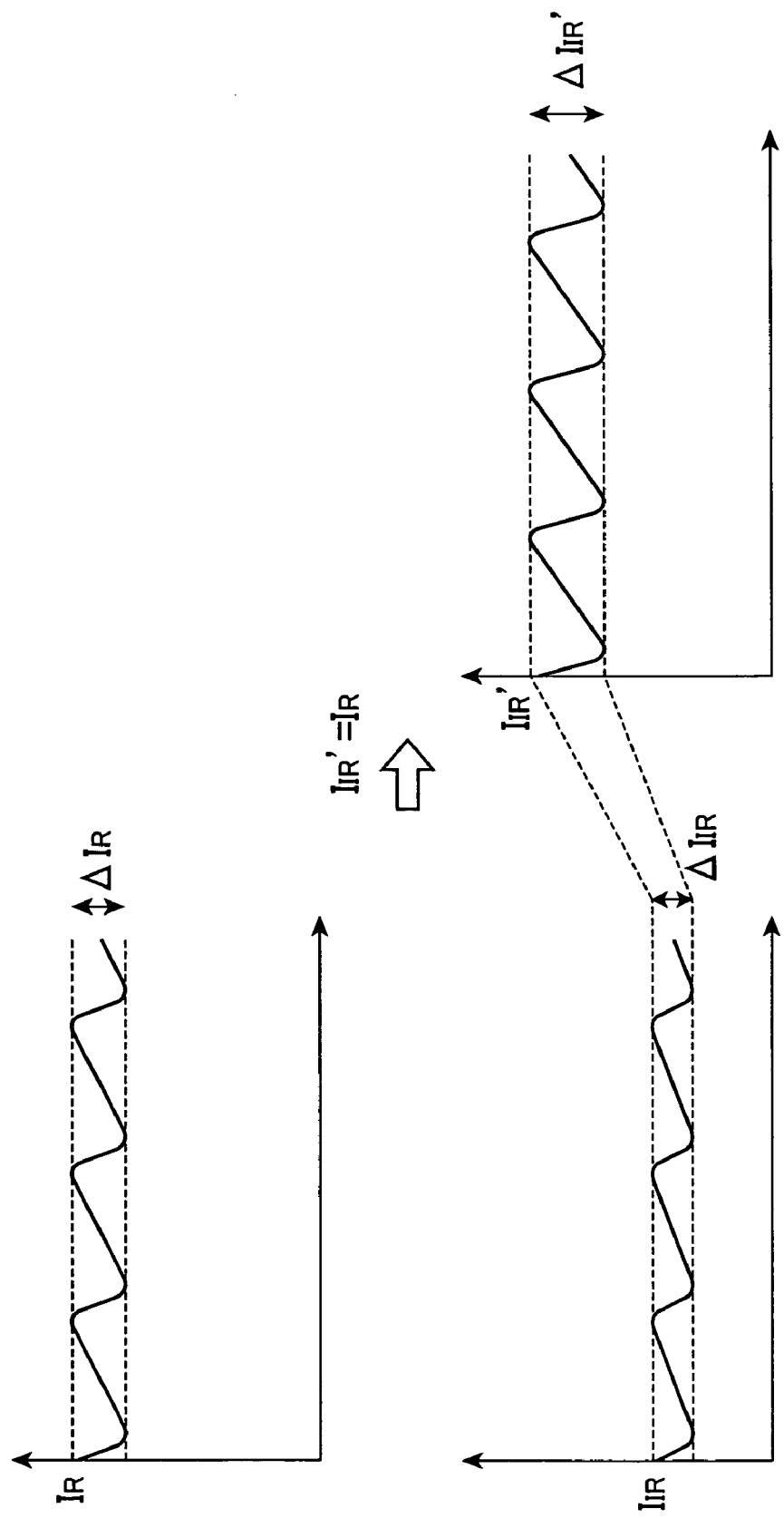

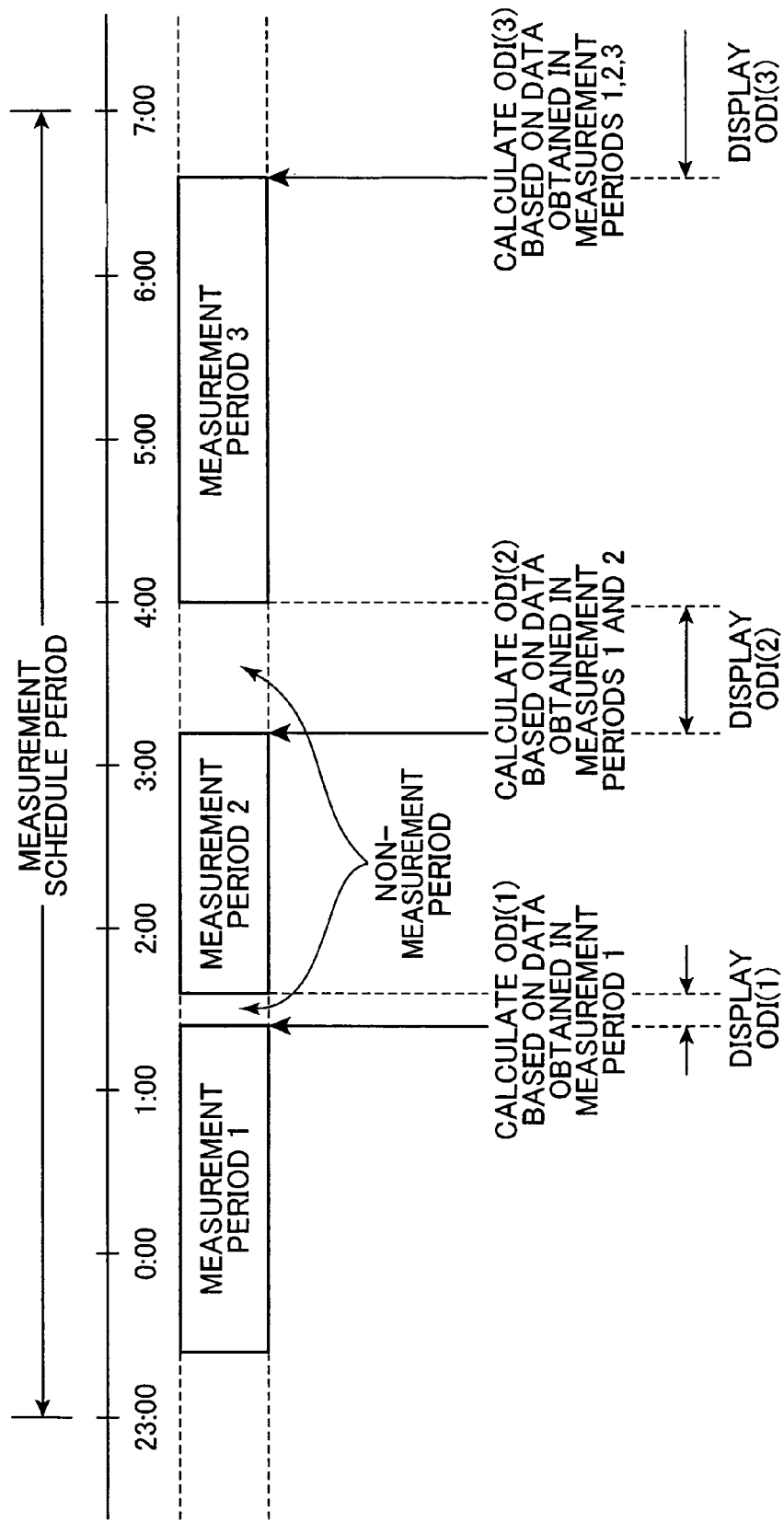

VITAL INFORMATION MEASURING DEVICE

This application is based on Japanese Patent Application No. 2005-317241 and No. 2006-264778 filed on Oct. 31, 2005, and Sep. 28, 2006 the contents of which are hereby incorporated by reference.

BACKGROUND OF THE INVENTION

1. Field of the Invention

The present invention relates to a vital information measuring device for measuring vital information such as an arterial blood oxygen saturation or a pulse rate.

2. Description of the Related Art

There is used a pulse oximeter in the field of diagnosing a sleep apnea syndrome (SAS) (see U.S. Pat. No. 4,955,379 corresponding to Japanese Unexamined Patent Publication No. 1-153139/1989, for instance). The pulse oximeter has a measuring unit which is detachably attached to a predetermined measurement site of a living body i.e. a subject. The measuring unit is constructed in such a manner that light is outputted toward the measurement site of the living body, and an oxygen saturation ($SpO_2$) in blood of the measurement site is measured based on the amount of light transmitted through or reflected from the measurement site.

Also, the pulse oximeter is communicable with an external device e.g. a personal computer incorporated with a predetermined program. For instance, when data concerning a blood oxygen saturation (hereinafter, called as "blood oxygen saturation data") obtained from a subject by overnight pulse oximetry is outputted from the pulse oximeter to the personal computer, the program in the personal computer is activated to calculate an ODI (Oxygen Desaturation Index), which represents a change in blood oxygen saturation with time, or the number of times when the blood oxygen saturation is lowered than a predetermined threshold value per unit time, based on an average of the measurement data.

In the conventional art, a user of the pulse oximeter is required to connect the pulse oximeter to the personal computer, and to designate an operation of acquiring the ODI using the personal computer. In this arrangement, the ODI cannot be promptly confirmed after the measurement is completed. Also, the above operation is cumbersome for the user.

SUMMARY OF THE INVENTION

In view of the above problems residing in the conventional examples, it is an object of the present invention to provide a vital information measuring device that allows a user of a pulse oximeter to promptly confirm an ODI after a measurement is completed without imposing the user to designate an operation of acquiring the ODI after the measurement is completed, using a personal computer.

An aspect of the invention is directed to a vital information measuring device including: a measuring unit for measuring certain vital information concerning a living body; a storage for storing therein a signal outputted from the measuring unit as measurement data; a vital information acquirer for acquiring a sleep apnea index based on the measurement data stored in the storage; a display section for displaying the sleep apnea index acquired by the vital information acquirer; and a device body for integrally mounting the measuring unit, the storage, the vital information acquirer, and the display section.

These and other objects, features and advantages of the present invention will become more apparent upon reading the following detailed description along with the accompanying drawing.

BRIEF DESCRIPTION OF THE DRAWING

FIG. 1 is a diagram showing an arrangement of a pulse oximeter as an example of a vital information measuring device embodying the invention.

FIGS. 2A and 2B are diagrams showing a mechanism for detecting a mounted state of a measuring unit onto a fingertip of a subject.

FIG. 7 is a diagram for explaining normalization of a transmitted light amount of infrared light.

FIG. 15 is a time chart to be used in the case where a scheduled measurement period is set.

DETAILED DESCRIPTION OF THE PREFERRED EMBODIMENTS

Figure 3:
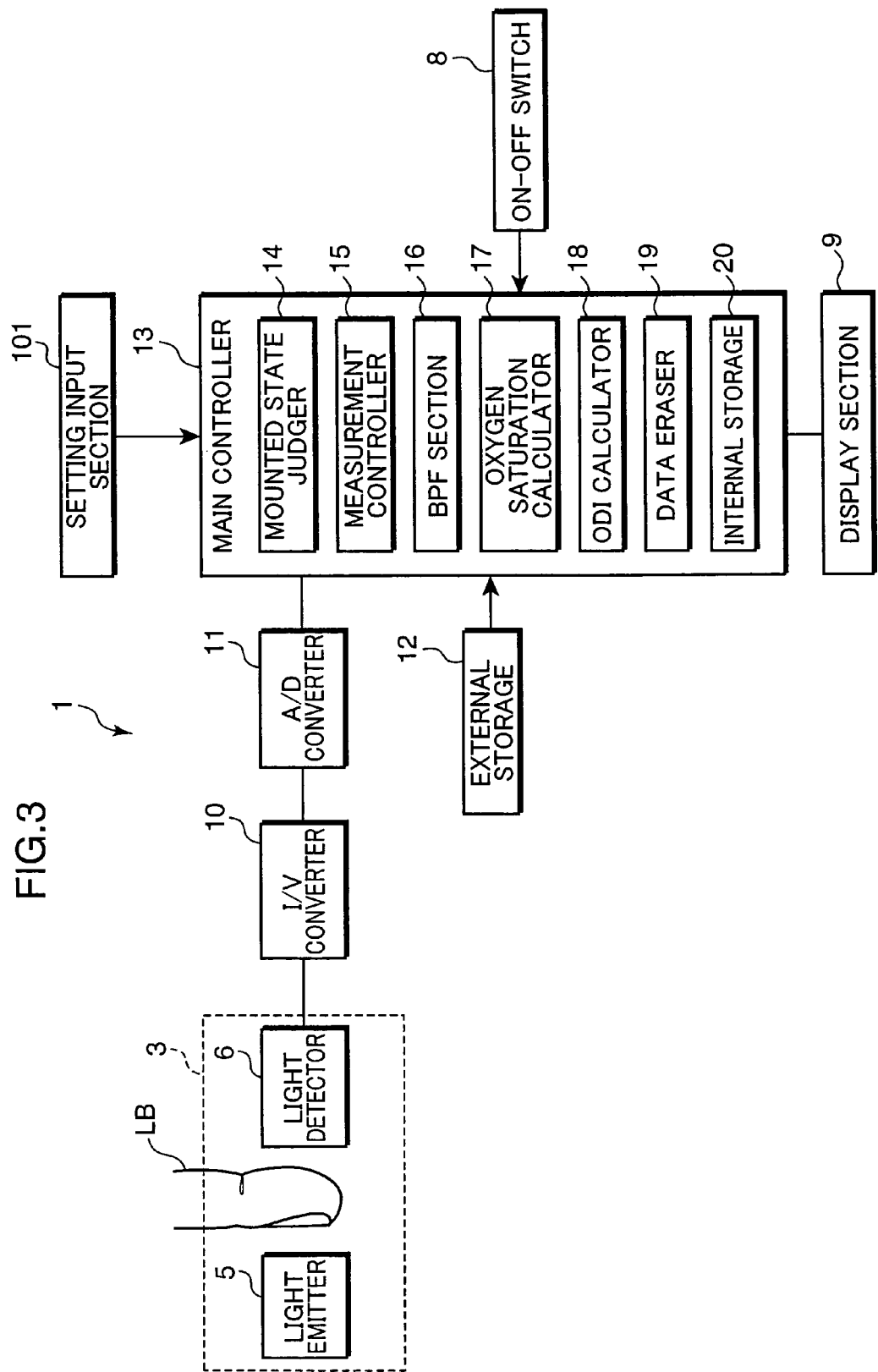
FIG. 3 is a block diagram showing an electrical configuration of the pulse oximeter.

A vital information measuring device as an embodiment of the invention is described referring to the drawings. FIG. 1 is a diagram showing an arrangement of a pulse oximeter, as an example of the vital information measuring device embodying the invention.

As shown in FIG. 1, the pulse oximeter 1 is designed to acquire a blood oxygen saturation based on an amount of light transmitted through or reflected from a measurement site of a living body. In this embodiment, a finger i.e. a fingertip of a subject is defined as the measurement site. The pulse oximeter 1 is a portable device including a rectangular parallelepiped device body 2, and a probe 3 which is electrically connected to the device body 2 by a cable 4. For sake of explanation, the arrangement of the probe 3 is described first.

The probe 3 has a paper-clip like shape capable of securely holding a measurement site e.g. a fingertip of a subject by a biasing force of a spring or a like member. Specifically, the probe 3 has a pair of holding pieces, and a light emitter 5 is provided on one of the holding pieces, and a light detector 6 is provided on the other one of the holding pieces. One ends of the holding pieces are interconnected to each other by a connecting member 7 in such a manner that the other ends thereof are openably closable. The light emitter 5 is a light source provided with an LED (Light Emitting Diode) for emitting red light R of a wavelength λ1 in a red light region, and an LED for emitting infrared light IR of a wavelength λ2 in an infrared light region. The probe 3 is an example of the measuring unit in the claimed invention.

The light detector 6 has a photoelectric conversion device e.g. a silicon photodiode for generating an electric current commensurate with an intensity of received light. In this embodiment, the light detector 6 has a sensitivity at least to the light of the wavelength λ1 and the light of the wavelength λ2. The light detector 6 receives light of the wavelengths λ1 and λ2 that have been transmitted through a living tissue LB of the subject. Arranging the LEDs on a common base member in proximity to each other enables to make optical paths of the light of two kinds to be transmitted through the living body substantially identical to each other, which makes detection conditions regarding the red light R and the infrared light IR substantially identical to each other.

The probe 3 in this embodiment is operated in such a manner that the light emitter 5 alternately emits the red light R of the wavelength λ1 and the infrared light IR of the wavelength λ2, and the light detector 6 performs a light detection in synchronism with the light emission of the light emitter 5, with the fingertip of the subject being securely held by the light emitter 5 and the light detector 6 in diagnosing an SAS in sleep. The light emission of the light emitter 5 and the light detection of the light detector 6 are controlled by a main controller 13 (see FIG. 3) to be described later. The light emission and the light detection with respect to the red light R and the infrared light IR are performed at a predetermined cycle e.g. in the range from 1/40 to 1/30 sec. Upon receiving the light, the light detector 6 outputs a current signal commensurate with the intensity of the received light to a current-voltage converter 10 (hereinafter, called as "I/V converter 10", see FIG. 3), provided in the device body 2, which will be described later.

As shown in FIG. 1 and FIG. 2A, an on-off switch 8 is provided at a predetermined position on an inner surface of the light emitter 5 to detect a mounted state of the probe 3 onto the fingertip of the subject. As shown in FIG. 2B, when the probe 3 is detachably attached to the fingertip, the on-off switch 8 is pressed against the fingertip. Thereby, an ON-state signal is outputted from the on-off switch 8 to supply an electric power from the device body 2 to the probe 3. On the other hand, when the probe 3 is detached from the fingertip, the pressing state of the on-off switch 8 by the fingertip is released. Thereby, an OFF-state signal is outputted from the on-off switch 8 to the device body 2 to suspend the supply of the electric power from the device body 2.

In this embodiment, the probe 3 is so designed that supply of an electric power from the device body 2 starts a measuring operation, and that suspending the power supply from the device body 2 terminates the measuring operation.

Referring back to FIG. 1, the device body 2 has a display section 9. Examples of the display section 9 are an LCD (Liquid Crystal Display), a 7-segment LED (Light Emitting Diode) display, an organic photoluminescent display, a CRT (Cathode Ray Tube) display, and a plasma display. The display section 9 displays data calculated by the main controller 13 to be described later. The display section 9 corresponds to a display section in the claimed invention.

The device body 2 includes an electric power supply section (not shown) such as a battery or a dry cell which is loaded in an unillustrated loading chamber. The display section 9, various circuits provided in the device body 2, and the probe 3 are driven upon receiving an electric power from the electric power supply section.

FIG. 3 is a block diagram showing an electrical configuration of the pulse oximeter 1. As shown in FIG. 3, the pulse oximeter 1 includes the probe 3, the on-off switch 8, the display section 9, a setting input section 101, the I/V converter 10, an analog-to-digital converter 11 (hereinafter, called as "A/D converter 11"), an external storage 12, and the main controller 13.

The probe 3, the on-off switch 8, and the display section 9 shown in FIG. 3 correspond to the probe 3, the on-off switch 8, and the display section 9 shown in FIG. 1, respectively.

The setting input section 101 as a setting information setter accepts setting of setting information relating to operations of the respective parts of the pulse oximeter 1, such as a measurement period, a point of time when a measurement is started, a measurement mode, a computation method, and a display format by the user including a person in charge of diagnosis e.g. a medical doctor, and a subject. The pulse oximeter 1 performs various operations based on the setting information supplied from the setting input section 101.

Generally, the setting information to be set by the user can be roughly classified into a kind of setting information belonging to a first setting area where an unauthorized change in setting information may obstruct the measurement, and a kind of setting information belonging to a second setting area where an arbitrary change of the setting information depending on a measurement environment is recommended. An example of the setting information in the first setting area is setting information concerning an object to be measured or a measurement condition, which is to be set by a person in charge of diagnosis such as a medical doctor depending on a diagnosis purpose. An example of the setting information in the second setting area is setting information which is recommended to be set by the subject himself or herself depending on a measurement environment such as the time when the subject normally falls asleep, or normal sleeping hours. In view of this, preferably, setting items belonging to the first setting area may be locked in performing the setting concerning the first setting area. For instance, an access authorization process such as entry of a password is required so that the subject is constrained from changing the setting information in the first setting area without permission. On the other hand, in performing the setting concerning the second setting area, the access authorization process is invalidated.

Alternatively, the person in charge of diagnosis may select setting information in the first setting area where the access authorization process is required. With this altered arrangement, an erroneous measuring operation can be securely prevented by allowing the subject to attach the pulse oximeter 1 only after the person in charge of diagnosis performs a setting concerning all the setting information, and locks the setting information. The access authorization process is not limited to entry of a password. For instance, setting on an area of the setting information to be locked, and selection of setting items to be locked may be executed with use of a specific personal computer or a like device which is externally connectable to the pulse oximeter 1.

The I/V converter 10 converts a current signal outputted from the light detector 6 at a predetermined cycle into a voltage signal to output the voltage signal to the A/D converter 11 as an analog photoelectric pulse wave signal. The A/D converter 11 converts the analog photoelectric pulse wave signal outputted from the I/V converter 10 into a digital photoelectric pulse wave signal to output the digital photoelectric pulse wave signal to the main controller 13.

Examples of the external storage 12 are a hard disk, a USB memory, a CD (Compact Disk), a DVD (Digital Versatile Disk), and a floppy Disk®. The external storage 12 stores therein data calculated by the main controller 13 such as blood oxygen saturation data, or pulse rate data obtained during a measurement period. The external storage 12 corresponds to a storage in the claimed invention.

The main controller 13 includes a microprocessor or a DSP (Digital Signal Processor). The main controller 13 calculates an arterial oxygen saturation based on the received photoelectric pulse wave signal in accordance with data or a program stored in an internal storage 20.

The main controller 13 functionally includes a mounted state judger 14, a measurement controller 15, a BPF (bandpass filter) section 16, an oxygen saturation calculator 17, an ODI calculator 18, a data eraser 19, and the internal storage 20.

The mounted state judger 14 judges that the probe 3 is detachably attached to the living body i.e. the fingertip of the subject when an ON-state signal is outputted from the on-off switch 8, and judges that the probe 3 is detached from the living body i.e. the fingertip of the subject when an OFF-state signal is outputted from the on-off switch 8. The mounted state judger 14 corresponds to the mounted state detector in the claimed invention, and the mounted state judger 14 and the on-off switch 8 constitute the mounted state detector in the claimed invention.

The measurement controller 15 controls the operations of the light emitter 5 and the light detector 6 of the probe 3 in accordance with a judgment result of the mounted state judger 14. In this embodiment, when the mounted state judger 14 judges that the probe 3 is detachably attached to the living body, the measurement controller 15 controls the light emitter 5 to alternately emit the red light R of the wavelength λ1, and the infrared light IR of the wavelength λ2 at a cycle of e.g. 1/40 sec. On the other hand, when the mounted state judger 14 judges that the probe 3 is detached from the living body, the measurement controller 15 controls the light emitter 5 and the light detector 6 to terminate the light emission and the light detection. The measurement controller 15 corresponds to the measurement controller in the claimed invention.

The BPF section 16 has a digital filter, and performs filtering with respect to a photoelectric pulse wave signal after an analog-to-digital conversion by the A/D converter 11. The BPF section 16 may include a digital low pass filter and a digital high pass filter, or include an FIR (Finite Impulse Response) filter.

The oxygen saturation calculator 17 calculates a blood oxygen saturation of the subject based on the amount of light detected by the light detector 6. Oxygen is transported by oxidation/reduction of hemoglobin in the blood. The hemoglobin has such optical characteristics that absorption of red light is decreased, and absorption of infrared light is increased when the hemoglobin is oxidized, and, conversely, absorption of red light is increased and absorption of infrared light is decreased when the hemoglobin is reduced. The oxygen saturation calculator 17 acquires information concerning a blood oxygen saturation i.e. an arterial oxygen saturation by measuring a change in transmitted light amounts of the red light and the infrared light, which are detected by the light detector 6, utilizing the optical characteristics.

Now, a principle as to how the oxygen saturation calculator 17 calculates the blood oxygen saturation using light is described.

Oxygen is transported to cells of a living body by way of hemoglobin (Hb) in blood. Hemoglobin (Hb) turns into oxidized hemoglobin (HbO$_2$) by bonding to oxygen in lungs, and the oxidized hemoglobin turns into hemoglobin again by consumption of the oxygen in the cells of the living body. The blood oxygen saturation i.e. SpO$_2$ represents a ratio of oxidized hemoglobin in blood, and is expressed by the following formula (1) where CHb is a concentration of hemoglobin, and CHbO$_2$ is a concentration of oxidized hemoglobin.

$$SpO_2\ (\%) = \frac{CHbO_2}{CHb + CHbO_2} \times 100 \tag{1}$$

Figure 4:
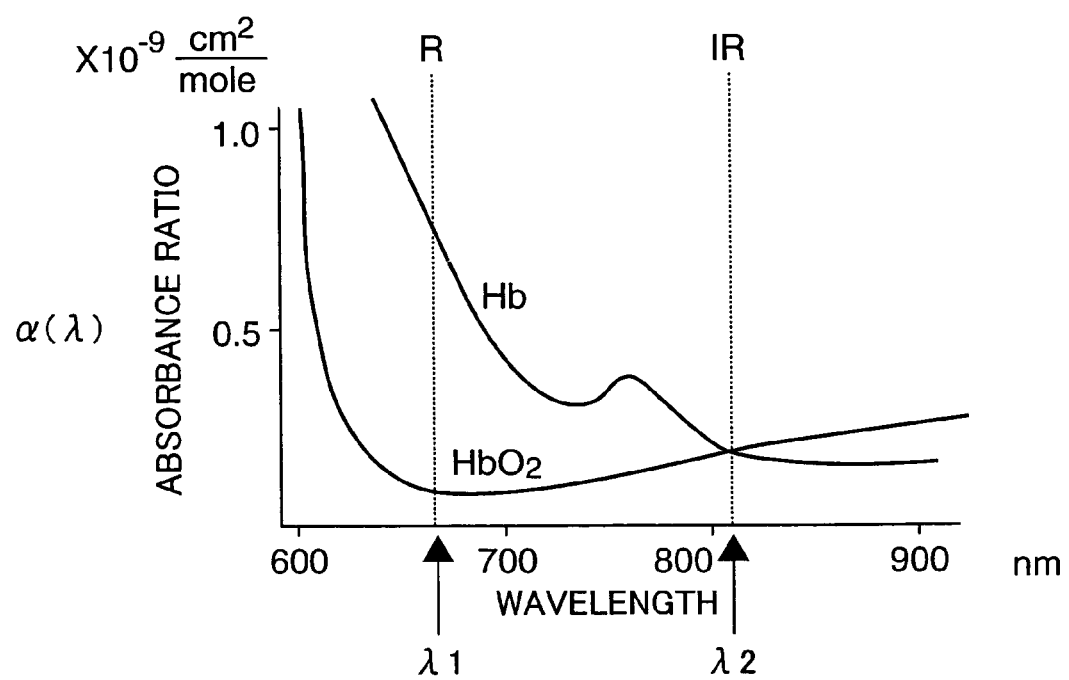
FIG. 4 is a graph showing absorption characteristics of hemoglobin and oxidized hemoglobin.

Absorbances of hemoglobin and oxidized hemoglobin are wavelength dependent. Absorbance indexes α(λ) of hemoglobin and oxidized hemoglobin have light absorption characteristics as shown in FIG. 4. The axis of abscissas in FIG. 4 represents a wavelength of light (unit: nm), and the axis of ordinate in FIG. 4 represents an absorbance index (unit: $10^{-9}$ cm$^2$/mole).

As shown in FIG. 4, hemoglobin and oxidized hemoglobin have different light absorption characteristics. Hemoglobin absorbs more light than oxidized hemoglobin with respect to the red light R of the wavelength λ1 in the red light region, but absorbs less light than the oxidized hemoglobin with respect to the infrared light IR of the wavelength λ2 in the infrared light region, which is out of the red light region. Specifically, for instance, assuming that the wavelength of the red light R is 660 nm where a difference in absorbance index between oxidized hemoglobin and hemoglobin is the largest, and the wavelength of the infrared light IR is 815 nm where absorbance indexes of oxidized hemoglobin and hemoglobin are identical to each other, the transmitted light amount of the infrared light IR does not change even if a ratio in amount of the oxidized hemoglobin versus the hemoglobin is changed. On the other hand, an increased amount of the hemoglobin decreases the transmitted light amount of the red light R, and an increased amount of the oxidized hemoglobin increases the transmitted light amount of the red light R. In other words, calculating a ratio of transmitted light amounts of the red light R versus the infrared light IR enables to obtain a blood oxygen saturation.

As mentioned above, the pulse oximeter 1 obtains the information concerning the blood oxygen saturation by utilizing a difference in light absorption characteristics between hemoglobin and oxidized hemoglobin with respect to the red light R and the infrared light IR. It should be noted that a pulse rate can be obtained by utilizing the difference in light absorption characteristics between hemoglobin and oxidized hemoglobin with respect to the red light R and the infrared light IR.

Figure 5A:
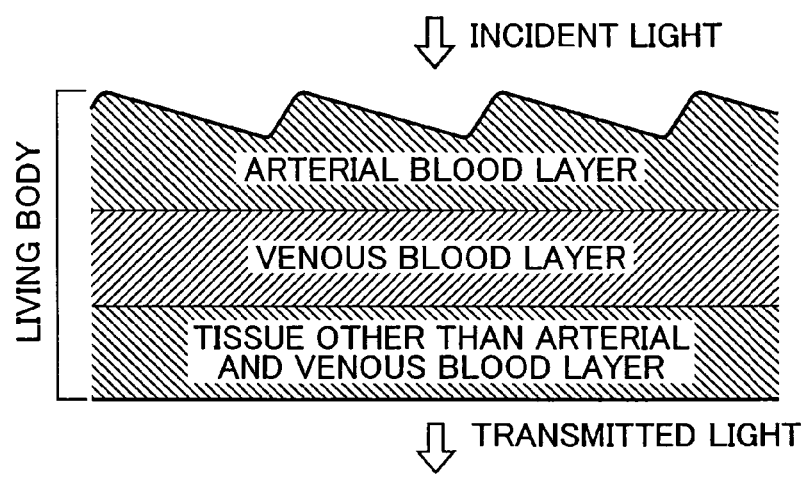
FIGS. 5A and 5B are diagrams showing light absorption with respect to a living body.

When light is irradiated onto a living body, a part of the light is absorbed into the living body, and the rest of the light is transmitted through the living body. The living body includes an arterial blood layer, a venous blood layer, and a tissue other than the arterial blood layer and the venous blood layer. As shown in FIG. 5A, light absorption in the living body includes absorption by the tissue other than the arterial blood layer and the venous blood layer, absorption by the venous blood layer, and absorption by the arterial blood layer. Since the tissue other than the arterial blood layer and the venous blood layer, and the venous blood layer do not change with time, the absorptions by these sites are substantially constant.

Figure 5B:
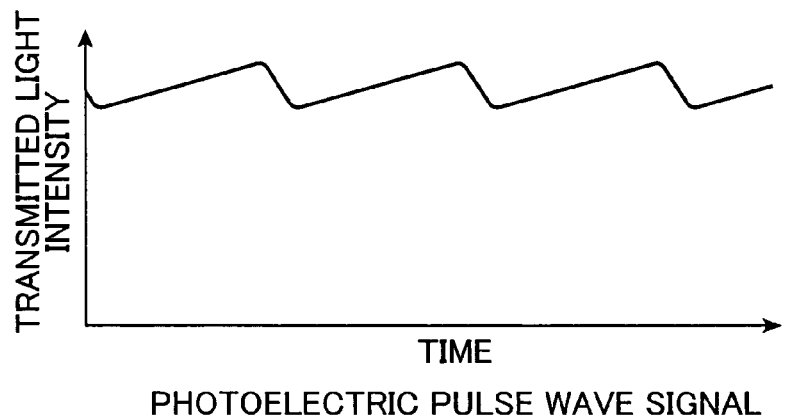

On the other hand, the arterial blood layer changes its diameter by a heartbeat. Since the diameter of the arterial blood layer is changed by the heartbeat, the light absorption by the arterial blood layer is changed with time by the heartbeat, as shown in FIG. 5B. In other words, it is conceived that a change in transmitted light intensity solely reflects a behavior of the arterial blood layer, and hardly includes an influence of the tissue other than the arterial blood layer and the venous blood layer, and an influence of the venous blood layer. Referring to FIG. 5B, the axis of abscissa represents a time, and the axis of ordinate represents a transmitted light intensity.

Figure 6A:
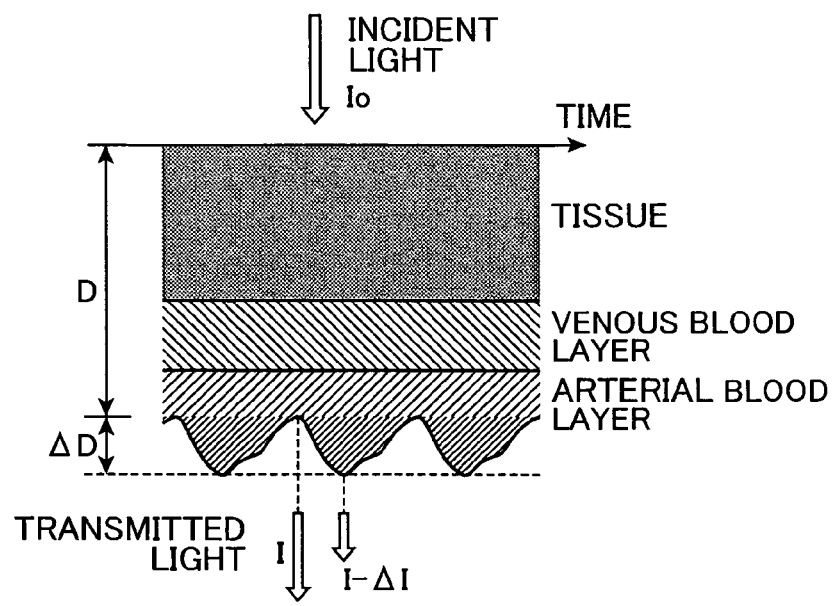
FIGS. 6A through 6C are diagrams schematically showing a relationship between incident light and transmitted light with respect to a living body.

In comparing a change in light amount between the red light R and the infrared light IR, it is necessary to cancel a difference in incident light amount between the red light R and the infrared light IR. FIG. 6A is a diagram schematically showing a relationship between light that is incident onto a living body, and light that is transmitted through the living body.

It is substantially difficult to make the incident light amount I0 onto the living body identical to each other between the red light R and the infrared light IR. Even if the incident light amount I0 is made identical between the red light R and the infrared light IR, it is impossible to compare solely a change in transmitted light intensity through the arterial blood layer between the red light R and the infrared light IR, because absorptive powers of the tissue other than the arterial blood layer and the venous blood layer, and of the venous blood layer are different between the red light R and the infrared light IR.

Figure 6B:
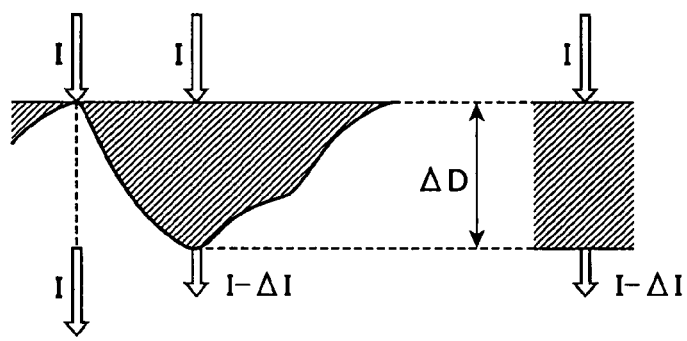
Figure 6C:
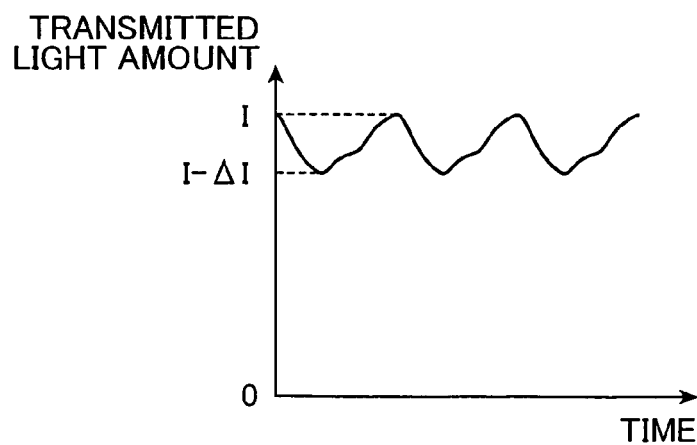

In view of the above, as shown in FIG. 6A, let it be assumed that a transmitted light amount through an arterial blood portion with a possible smallest diameter i.e. a possible largest transmitted light amount is defined as "I", and a transmitted light amount through an arterial blood portion with a possible largest diameter i.e. a possible smallest transmitted light amount is defined as (I−ΔI). Then, as shown in FIGS. 6B and 6C, transmitted light with the light amount (I−ΔI) is supposed to be obtained if light with the light amount "I" is irradiated onto an arterial blood layer with a thickness ΔD.

Then, as shown in FIG. 7, normalization is conducted to make a transmitted light amount $I_R$ of the red light R coincident with a transmitted light amount $I_{IR}$ of the infrared light IR. Specifically, by conducting normalization to satisfy an equation: $I_{IR}' = I_R$ where $I_{IR}'$ corresponds to the transmitted light amount $I_{IR}$, a ratio of a change in light amount with respect to the arterial blood layer between the red light R and the infrared light IR is calculated, i.e. an equation: $(\Delta I_R/I_R)/(\Delta I_{IR}/I_{IR})$ is implemented, whereby a blood oxygen saturation is calculated.

A relationship of incident light versus reflected light can be expressed by the following formula (2) according to the Lambert Beer rule.

$$\log\left(\frac{I}{I - \Delta I}\right) = EC\Delta D \quad (2)$$

where E is an absorbance index of an absorptive object, and C is a concentration of the absorptive object.

Substituting the wavelengths of the red light R and the infrared light IR in the formula (2), respectively, specifically, substituting $I_R$ and $I_{IR}$ for I in the formula (2), respectively, and obtaining a ratio of the resultant two formulae enables to yield the following formula (3).

$$\frac{\log\{I_R/(I_R - \Delta I_R)\}}{\log\{I_{IR}/(I_{IR} - \Delta I_{IR})\}} = \frac{E_R C \Delta D}{E_{IR} C \Delta D} = \frac{E_R}{E_{IR}} \quad (3)$$

where $I_R$ is a transmitted light amount of red light R, $I_{IR}$ is a transmitted light amount of infrared light IR, $E_R$ is an absorbance index of the red light R, and $E_{IR}$ is an absorbance index of the infrared light IR.

Figure 8:
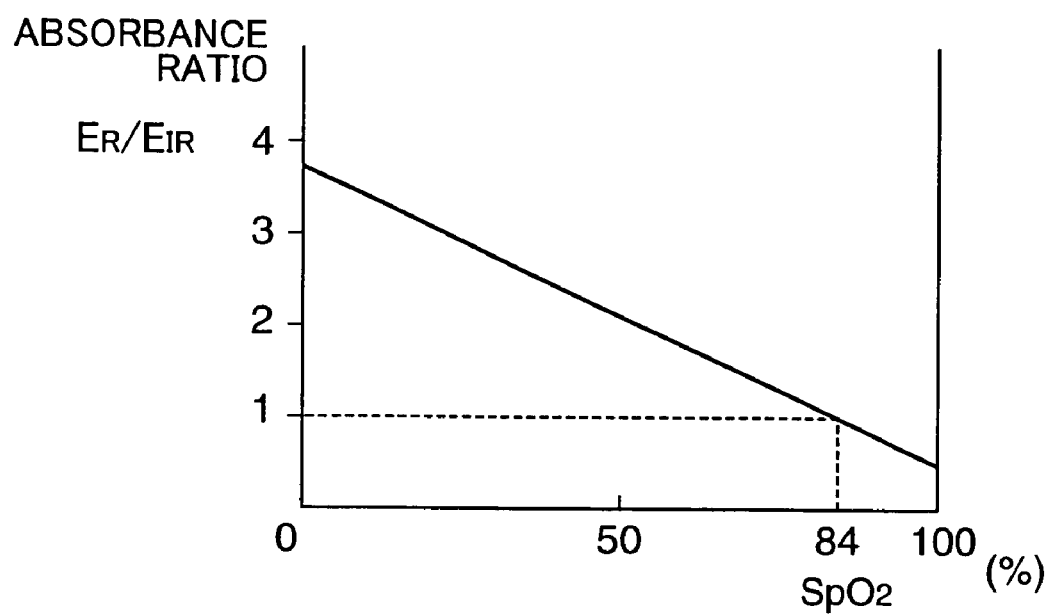
FIG. 8 is a graph showing a relationship between an absorbance ratio and a blood oxygen saturation.

FIG. 8 is a graph showing a relationship between an absorbance ratio ($E_R/E_{IR}$), and a blood oxygen saturation i.e. $SpO_2$ in the case where the wavelengths of the red light R and the infrared light IR are 660 nm and 815 nm, respectively. As shown in FIG. 8, the blood oxygen saturation i.e. $SpO_2$ is increased in proportion to lowering of the absorbance ratio ($E_R/E_{IR}$). The oxygen saturation calculator 17 stores the thus calculated blood oxygen saturation data into the external storage 12.

Referring back to FIG. 3, the ODI calculator 18 calculates an ODI (Oxygen Desaturation Index), which is an index relating to the number of times when the blood oxygen saturation is lowered than a predetermined threshold value per unit time, using the blood oxygen saturation data stored in the external storage 12, upon completion of a measurement of the blood oxygen saturation. The ODI is a ratio of the number of times when the blood oxygen saturation is lowered than the threshold value relative to the number of measurements of the blood oxygen saturation per unit time in terms of percentage. The ODI corresponds to the sleep apnea index in the claimed invention.

There is a case that the probe 3 may be inadvertently detached from the subject's fingertip during overnight pulse oximetry, and thereafter the subject may re-attach the probe 3. Also, there is a case that the subject may be awakened during overnight pulse oximetry for nature's call or a like event, temporarily detach the measurement unit 3, and re-attach the measurement unit 3. In such cases where the probe 3 is temporarily detached inadvertently or intentionally for a relatively short period, there exists a measurement interruption period when the measuring operation of the blood oxygen saturation is temporarily interrupted in this embodiment. This is because start and termination of the measuring operation of the probe 3 are controlled based on a mounted state of the probe 3 in this embodiment.

In view of the above, this embodiment adopts an arrangement, in which an ODI is calculated, using the blood oxygen saturation data that has been acquired until the measuring operation is temporarily interrupted, for display of the calculation result on the display section 9 during the measurement interruption period, and an ODI is calculated, using the blood oxygen saturation data that have been acquired by the respective consecutive measuring operations before and after the measurement interrupt period when the measuring operation is resumed after the measurement interruption, and after the measurement is completed, for display of the calculation result on the display section 9. The measurement interruption period corresponds to the non-measurement period in the claimed invention.

Figure 9:
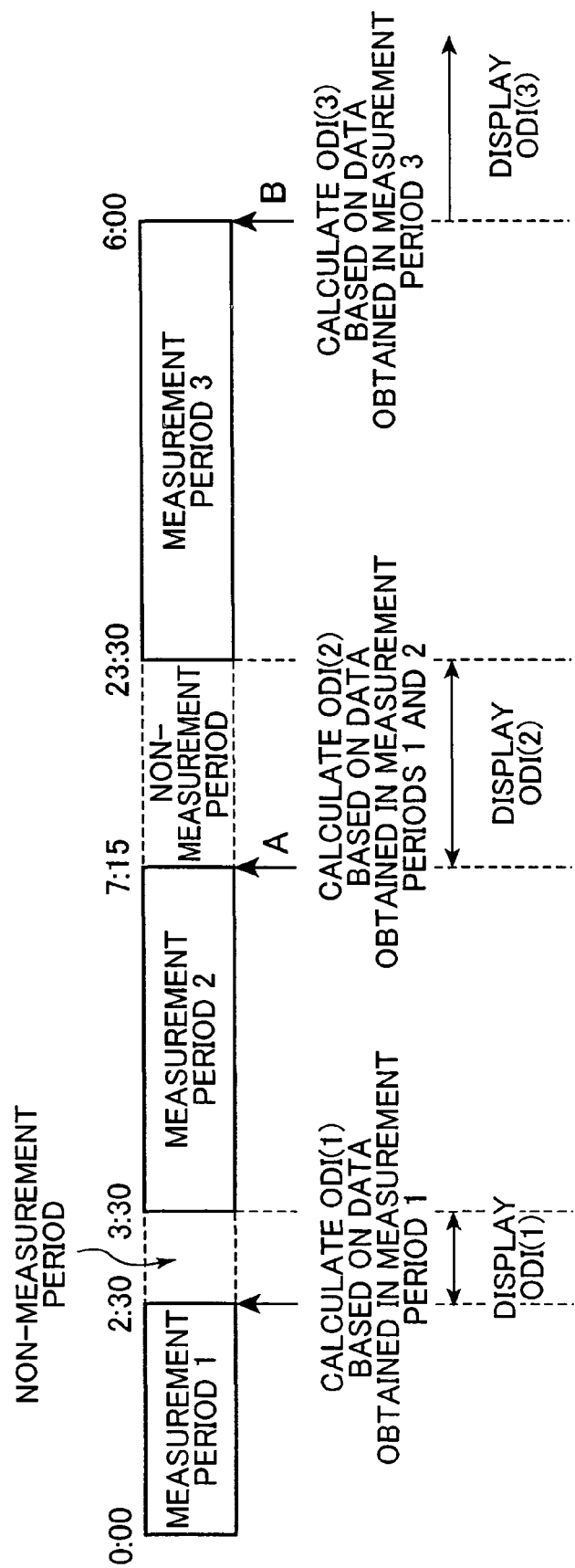
FIG. 9 is a time chart for explaining an approach of calculating an ODI.

For instance, as shown in FIG. 9, let it be assumed that a measurement is started at 12:00 a.m. (midnight) when the subject falls asleep, the probe 3 is detached from the subject's fingertip at 02:30 a.m., the probe 3 is re-attached at 03:30 a.m., and then the subject gets up at 07:15 a.m. when the sleep is terminated and the measurement is completed.

In the above event, the ODI calculator 18 reads the blood oxygen saturation data that has been acquired in a measurement period 1 from 12:00 a.m. to 02:30 a.m. out of the external storage 12 for calculation of an ODI, and displays the calculated ODI on the display section 9 in a period from 02:30 a.m. to 03:30 a.m. Then, the ODI calculator 18 calculates an ODI, using the blood oxygen saturation data that has been acquired in the measurement period 1, and the blood oxygen saturation data that has been acquired in a measurement period 2 from 03:30 a.m. to 07:15 a.m., and displays the calculated ODI on the display section 9 in a period from 07:15 a.m. to a point of time when a next measuring operation is started.

Thus, the ODI calculator 18 calculates the ODI based on the blood oxygen saturation data that have been acquired substantially overnight. This enables to obtain accurate ODI data, as ODI data to be calculated and displayed during the period from 07:15 a.m. to the point of time when the next measuring operation is started, as compared with a case that an ODI is calculated, merely using the blood oxygen saturation data obtained in the measurement period 2. The oxygen saturation calculator 17 and the ODI calculator 18 constitute the vital information acquirer in the claimed invention.

Displaying the ODI based on the measurement data that has been acquired until the measurement interruption during the measurement interruption period in the course of a series of measuring periods corresponding to an overnight is not only advantageous in providing the subject with interim data concerning the ODI, but also advantageous in notifying the subject of an abnormality on measurement if a normal measurement is not conducted resulting from occurrence of the abnormality. With the notification, the subject is allowed to execute the measurement after the measurement interruption, after correcting the abnormality on measurement. Also, the above arrangement is advantageous in the case where the subject is awakened e.g. in the middle of the night, and measurement is interrupted. In such a condition, the subject is allowed to record and confirm the ODI that has been calculated based on the measurement data acquired until the measurement interruption, and then, to compare the ODI with the ODI that has been calculated based on the measurement data acquired after the measurement interruption until the series of measurements has been completed on the next day. This allows for comparison, analysis, and a like operation concerning a correlation between subjective symptoms in the former half period and the latter half period of the overnight sleep, and the actually acquired vital information.

In the case where the subject is temporarily awakened due to some reason, intentionally detaches the pulse oximeter 1, and re-attaches the pulse oximeter 1, the above arrangement enables to record the points of time when the respective events happened, and to continue the measurement regardless of the events. This allows the user to know the timing of awakening, or compare and study concerning a correlation between the awakening and the vital information, which enables to obtain more effective data. Also, in the above arrangement, attachment of the probe 3 serves as a switch for starting a measurement. This eliminates an unwanted interruption of measurement in response to, for instance, depressing of a switch, which results from rolling over of the subject or a like movement. Furthermore, the arrangement enables to record the point of time when the measurement has been started by attachment of the probe 3, which is easily executable by the subject's groping with a hand, for instance. This provides enhanced operability in a condition that the subject is half awakened and half unconscious during the sleep.

In the above arrangement, the sum of the measurement data acquired in the measurement period 1 and in the measurement period 2 is stored in the external storage 12 as final blood oxygen saturation data, and the ODI is calculated by reading the sum data out of the external storage 12 for displaying the ODI. Additionally, the blood oxygen saturation data acquired in the measurement period 1 as the first measurement period, and the blood oxygen saturation data acquired in the measurement period 2 as the second measurement period may be individually stored in the external storage 12. The altered arrangement enables to individually acquire the ODI in the measurement period 1, the ODI in the measurement period 2, and the ODI in the series of measurement periods, with the non-measurement period being in between the measurement period 1 and the measurement period 2.

In the example shown in FIG. 9, the measurement interruption period is one hour from 02:30 a.m. to 03:30 a.m. If the measurement interruption period is unduly long, it may be improper to handle a measurement period including the unduly long measurement interruption period as a series of measurement periods. In view of this, the setting input section 101 predefines an allowable maximal length of the measurement interruption period which enables to regard the measurement after the measurement interruption as a part of the series of measurements in a range from about thirty minutes to about two hours and a half. Alternatively, the allowable maximal length of the measurement interruption period may be arbitrarily set by 30 minutes by the user, using the setting input section 101.

A suspension mode of prohibiting continuous measurement after a measurement interruption may be additionally provided. The suspension mode is usable e.g. in using an ODI that has been calculated based on the measurement data in a first sleep period after the subject falls asleep for the first time and until the subject wakes up next time, as assessment data. In this case, a one-time continuous measurement period is regarded as a series of measurements. The series of measurements can be conducted without providing the suspension mode unless the subject re-attaches the pulse oximeter 1 after having woken up in the course of the measurement and detached the pulse oximeter 1. However, providing the suspension mode allows for acquiring the ODI in the first sleep period even if the subject has inadvertently re-attached the pulse oximeter 1 after the measurement interruption.

The data eraser 19 erases the blood oxygen saturation data stored in the external storage 12 if a measurement is not conducted for a predetermined time i.e. a data unerasable period. The data eraser 19 has an unillustrated timer. The main controller 13 controls the timer to start measuring a time if the mounted state judger 14 judges that the probe 3 is detached from the subject's fingertip i.e. the mounted state is released. Then, the data eraser 19 erases the blood oxygen saturation data stored in the external storage 12 if the time measured by the timer has reached a predetermined point of time. The data eraser 19 constitutes the judger in the claimed invention, and also corresponds to the data eraser in the claimed invention.

The aforementioned data unerasable period is set to a relatively long time to discriminate a condition that the aforementioned measurement interruption has occurred from a condition that the measurement has been completed i.e. the subject's sleep has terminated. Based on an assumption that the non-measurement period from completion of the current overnight pulse oximetry to start of a next overnight pulse oximetry is fifteen hours, and the measurement interruption period is one to two hours based on a premise that the measurement interruption period is considerably shorter than the non-measurement period, the data unerasable period is set to eight hours, for instance. The data unerasable period may be arbitrarily set by the user, using the setting input section 101.

With this arrangement, in the example shown in FIG. 9, assuming that the next overnight pulse oximetry is started at 11:30 p.m. on this day, the data eraser 19 erases the blood oxygen saturation data that have been acquired in the measurement periods 1 and 2 at 03:15 p.m. on this day upon lapse of eight hours from 07:15 a.m. at the termination of the current overnight pulse oximetry, because the eight hours has elapsed at 03:15 p.m. from the wake-up time of 07:15 a.m. when the probe 3 is detached from the fingertip. This eliminates likelihood that an ODI may be calculated, including the blood oxygen saturation data that has been acquired in the day before the current overnight pulse oximetry.

Now, assuming that the next overnight pulse oximetry is completed at 06:00 a.m., which is now this day, without interruption of the measurement. Then, the ODI calculator 18 calculates an ODI, using the blood oxygen saturation data that has been acquired in a period from 11:30 p.m. on the previous day to 06:00 a.m. on this day.

On the other hand, the measurement interruption period i.e. the non-measurement period from 02:30 a.m. to 03:30 a.m. on the previous day is shorter than the eight hours. Accordingly, there is no likelihood that the blood oxygen saturation data that has been acquired in the measurement period 1 from 12:00 a.m. to 02:30 a.m. may be erased due to the existence of the measurement interruption period.

Alternatively, the data eraser 19 may be provided with a function of erasing the blood oxygen saturation data i.e. raw measurement data based on which an ODI is calculated, in response to calculation of the ODI and storage of the calculated ODI into the external storage 12. The altered arrangement enables to remarkably save the storage capacity of the external storage 12, and to perform a long-term measurement without performing an erasing operation of the data or transferring operation of the data. A point of time when data is erased can be arbitrarily set. For instance, a point of time immediately after the ODI is calculated, or a certain point of time before the pulse oximeter 1 enters a measurement period in the case where the measurement period is defined based on a specific point of time, as mentioned above, may be defined as the data erasing point of time.

The internal storage 20 may include an EEPROM (Electrically Erasable and Programmable Read Only Memory), and stores a program or data so that the main controller 13 can compute an arterial oxygen saturation based on a photoelectric pulse wave signal.

Figure 10:
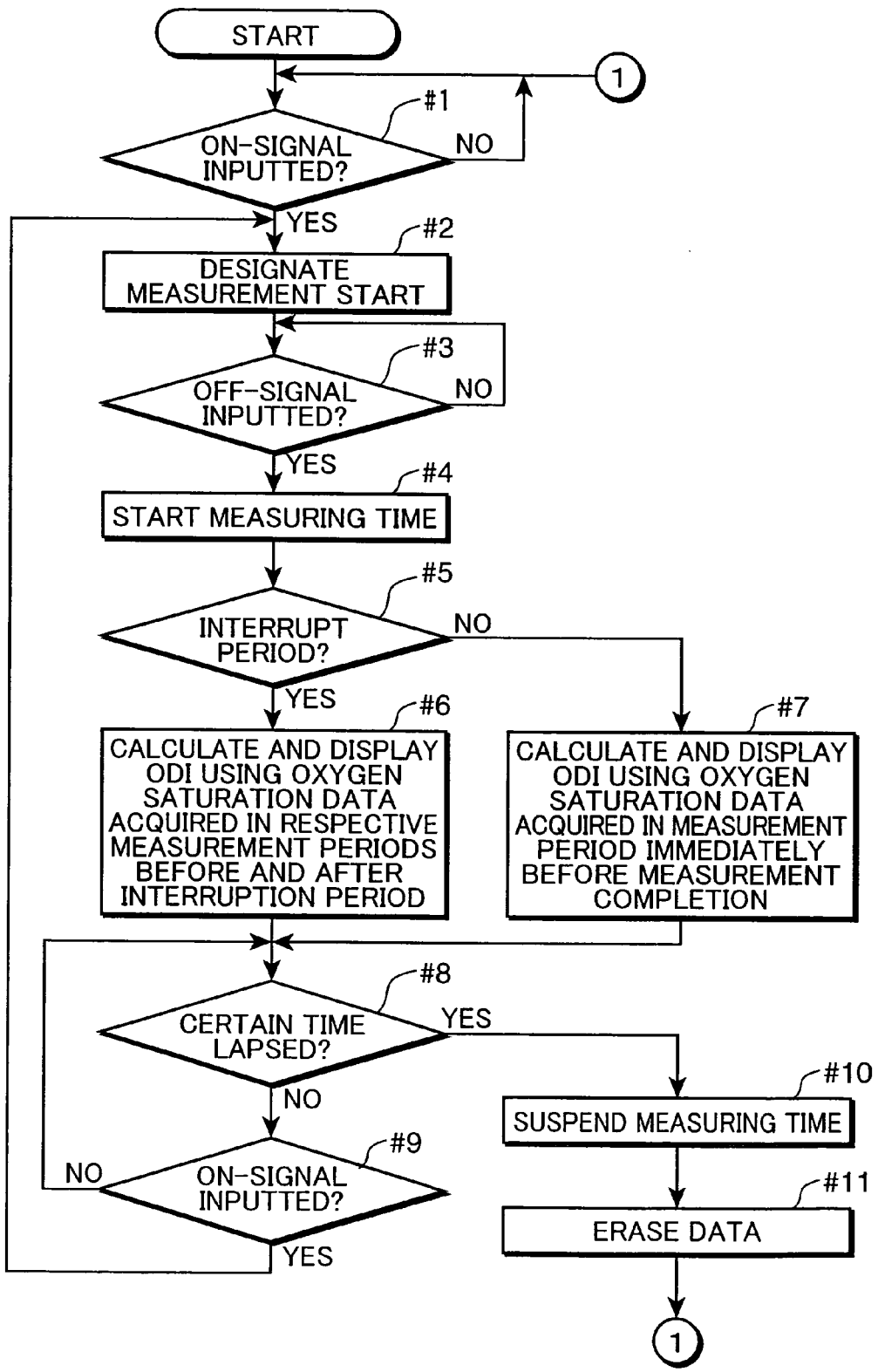
FIG. 10 is a flowchart showing a measuring operation to be executed by the pulse oximeter.

FIG. 10 is a flowchart showing a measuring operation to be executed by the pulse oximeter 1. The description is made based on a premise that the pulse oximeter 1 is used for the first time in a state that no data is stored in the external storage 12.

Referring to FIG. 10, upon receiving an ON-state signal from the on-off switch 8, (YES in Step #1), the main controller 13 controls the probe 3 to start a measuring operation (Step #2). Thereby, the probe 3 executes an emission operation and a detection operation of the red light R of the wavelength λ1 and the infrared light IR of the wavelength λ2 at a predetermined cycle, and stores acquired blood oxygen saturation data into the external storage 12.

Then, the main controller 13 judges whether an OFF-state signal is outputted from the on-off switch 8 (Step #3). If it is judged that the OFF-state signal is not outputted (NO in Step #3), the main controller 13 waits. If it is judged that the OFF-state signal is outputted (YES in Step #3), the timer starts measuring a time (Step #4).

Next, the main controller 13 judges whether the measuring operation of the probe 3 has been interrupted (Step #5). If the main controller 13 judges that the measuring operation has been interrupted (YES in Step #5), the main controller 13 controls the ODI calculator 18 to calculate an ODI, using the blood oxygen saturation data that have been acquired in the respective consecutive measuring periods before and after the measurement interruption period, and controls the display section 9 to display the calculated ODI (Step #6). Step #6 corresponds to a process to be executed at 07:15 a.m. indicated by the arrow A in FIG. 9, for instance.

If, on the other hand, the main controller 13 judges that the measuring operation has not been interrupted (NO in Step #5), the main controller 13 controls the ODI calculator 18 to calculate an ODI, using the blood oxygen saturation data acquired in the measuring period that has elapsed until immediately before the measurement completion, and controls the display section 9 to display the calculated ODI (Step #7). Step #7 corresponds to a process to be executed at 06:00 a.m. indicated by the arrow B in FIG. 9.

Then, the main controller 13 judges whether the timer has measured the predetermined time (Step #8). If the main controller 13 judges that the timer has not measured the predetermined time (NO in Step #8), the main controller 13 judges whether an ON-state signal is outputted from the on-off switch 8 (Step #9). If the main controller 13 judges that the ON-state signal is not outputted from the on-off switch 8 (NO in Step #9), the routine returns to Step #8. If, on the other hand, the main controller 13 judges that the ON-state signal is outputted from the on-off switch 8 e.g. at 03:30 a.m. in FIG. 9 (YES in Step #9), the routine returns to Step #2.

If the main controller 13 judges that the timer has measured the predetermined time (YES in Step #8), the main controller 13 controls the timer to suspend its time measuring operation (Step #10), and controls the data eraser 19 to erase the blood oxygen saturation data stored in the external storage 12 (Step #11).

As mentioned above, the pulse oximeter 1 is provided with the function of calculating an ODI using the measured blood oxygen saturation, and of displaying the calculation result on the display section 9. This allows the user to confirm the ODI immediately after the measurement completion without imposing the user to designate an operation of acquiring the ODI after the measurement completion, using a personal computer, as required in the conventional art.

Also, the on-off switch 8 is provided to detect a mounted state of the probe 3 onto a living body, and to allow the probe 3 to automatically start and terminate a measuring operation depending on the detected mounted state of the probe 3. This eliminates the requirement that the user should enter designation on start and termination of a measuring operation of the probe 3 in starting the measuring operation, which provides enhanced operability of the pulse oximeter 1. Also, in use of the pulse oximeter in which the user is requested to enter designation on start and termination of a measuring operation of the probe 3 in starting the measuring operation, the above arrangement eliminates a drawback that data acquisition is failed due to the user's neglect of entering designation on start of a measuring operation, or that a measuring operation is conducted in an unwanted measurement period due to the user's neglect of entering designation on termination of the measuring operation, which may result in calculation of an ODI, using measurement data including unwanted blood oxygen saturation data.

Further, the timer starts measuring a time upon detection of intentional or inadvertent detachment of the probe 3 from the subject's fingertip. If the probe 3 is re-attached to the fingertip before the time measured by the timer reaches the predetermined time i.e. if the measuring operation is interrupted, the ODI is calculated, using all the blood oxygen saturation data that have been acquired in the respective consecutive measuring periods before and after the measurement interruption period. This enables to obtain accurate ODI data.

Furthermore, the blood oxygen saturation data stored in the external storage 12 is erased if the time measured by the timer has reached the predetermined time without re-attachment of the probe 3 onto the subject's fingertip. This enables to minimize a storage capacity required for the external storage 12, and to eliminate a manual data erasing operation by the user, which provides enhanced operability of the pulse oximeter 1.

The following modifications (1) through (6) may be applied to the invention in addition to or in place of the foregoing embodiment.

Figure 11A:
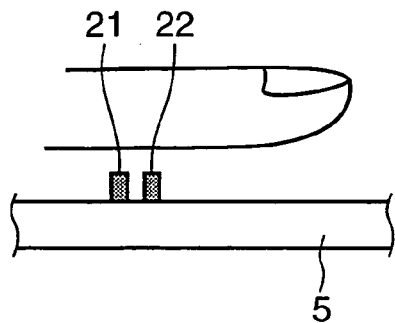
FIGS. 11A and 11B are diagrams showing a modified arrangement of a mechanism for detecting a mounted state of the measuring unit onto a fingertip of a subject.
Figure 11B:
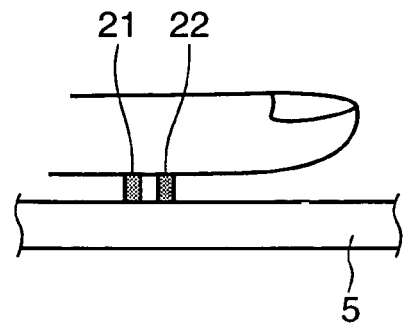

(1) The foregoing embodiment adopts the on-off switch 8 as a mechanism for detecting a mounted state of the probe 3 onto a fingertip of a living body. Alternatively, as shown in FIGS. 11A and 11B, two electrodes 21 and 22 may be provided at predetermined positions on the light emitter 5 or the light detector 6, and attachment of the probe 3 onto the fingertip may be detected by a current flow between the electrodes 21 and 22 via the fingertip upon the attachment of the probe 3 onto the fingertip, and detachment of the probe 3 from the fingertip may be detected by suspension of the current flow between the electrodes 21 and 22 upon the detachment of the fingertip from the electrodes 21 and 22.

Figure 12A:
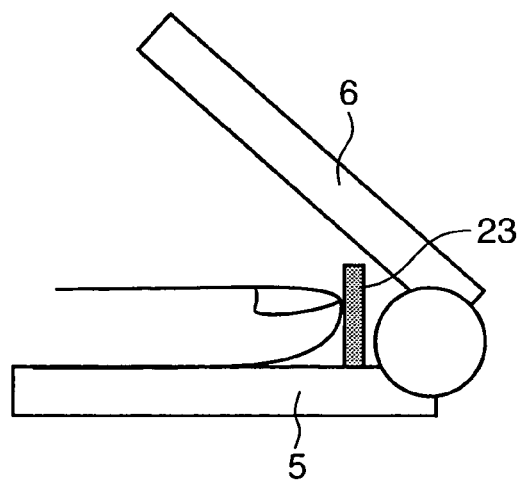
FIGS. 12A and 12B are diagrams showing another modified arrangement of a mechanism for detecting a mounted state of the measuring unit onto a fingertip of a subject.
Figure 12B:
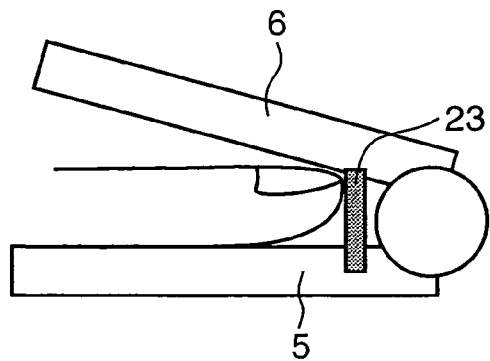

The foregoing embodiment adopts the on-off switch 8 which is operable by pushing against the subject's fingertip. Unlike the probe 3 in the embodiment constructed such that the light emitter 5 and the light detector 6 are urged toward each other so that the fingertip is held between the light emitter 5 and the light detector 6, an arrangement as shown in FIGS. 12A and 12B may be used, in the case where a measuring unit is constructed in such a manner that one ends of holding pieces i.e. a light emitter 5 and a light detector 6 are urged away from each other, and the fingertip is fixed by the holding pieces in a state that the light emitter 5 and the light detector 6 hold the fingertip with use of a certain member in attaching the measuring unit onto the fingertip. Specifically, the arrangement uses an on-off switch 23 which is operable by movements of the holding pieces toward and away from each other i.e. opening and closing operations of the probe 3.

For instance, in the modified measuring unit, the on-off switch 23 is provided at a predetermined position on the light emitter 5, and the holding piece corresponding to the light detector 6 turns the on-off switch 23 to an ON-state when the distance between the light emitter 5 and the light detector 6 is smaller than a predetermined value resulting from holding of the fingertip between the light emitter 5 and the light detector 6 in attaching the probe 3. Thereby, the probe 3 is judged to be attached to the fingertip.

The point of time when the measuring operation of the probe 3 is terminated may be a point of time when the ON-state of the on-off switch 23 is released resulting from increase of the distance between the holding pieces corresponding to the light emitter 5 and the light detector 6 over the predetermined value, or be a point of time when a detected light amount of the light detector 6 is lower than a predetermined level, utilizing a phenomenon that the detected light amount of the light detector 6 is decreased as the distance between the light emitter 5 and the light detector 6 is increased.

Figure 13A:
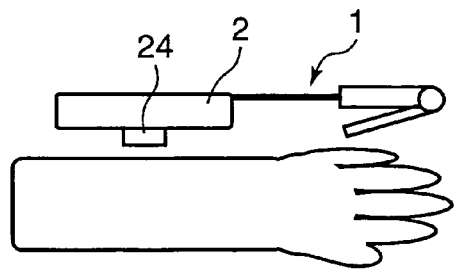
FIGS. 13A and 13B are diagrams showing yet another modified arrangement of a mechanism for detecting a mounted state of the measuring unit onto a fingertip of a subject.
Figure 13B:
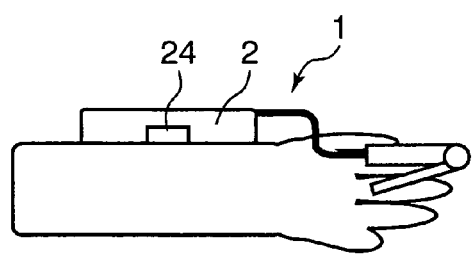

As a further altered form, as shown in FIG. 13A, in which the device body 2 is designed to be mounted on the living body e.g. an arm of a subject, the pulse oximeter 1 may be constructed as follows. Specifically, an on-off switch 24 equivalent to the on-off switch 23 in the modified embodiment is arranged at a predetermined position of the device body 2 at which the device body 2 is firmly contacted with the living body in attachment. As shown in FIG. 13B, attachment of the pulse oximeter 1 onto the living body is detected by turning on of the on-off switch 24 upon the attachment of the pulse oximeter 1 onto the living body, and as shown in FIG. 13A, detachment of the pulse oximeter 1 from the living body is detected by release of the ON-state of the on-off switch 24 upon the detachment of the pulse oximeter 1 from the living body.

Figure 14A:
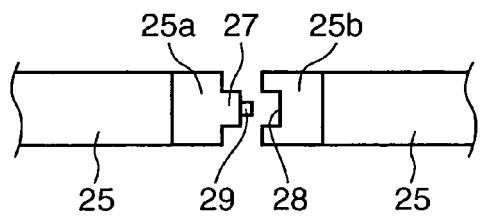
FIGS. 14A and 14B are diagrams showing still another modified arrangement of a mechanism for detecting a mounted state of the measuring unit onto a fingertip of a subject.
Figure 14B:
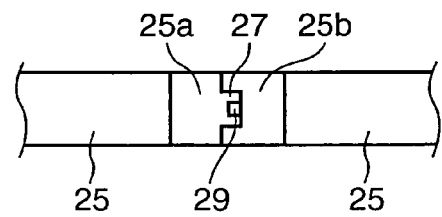

As a yet further altered form, in use of a pulse oximeter constructed such that a device body is mounted around a part of a living body e.g. an arm or a wrist of a subject by winding a fastening belt around the arm or the wrist of the subject, the following arrangement may be proposed. Specifically, as shown in FIG. 14A, an on-off switch 29 equivalent to the on-off switch 8, 24 is arranged at a predetermined position on a protrusion 27 formed at one end 25a of a fastening belt 25. As shown in FIG. 14B, the on-off switch 29 is turned on when the fastening belt 25 is wound around the part of the living body in attaching the pulse oximeter 1 onto the living body, with engagement of the protrusion 27 into a recess 28 formed in the other end 25b of the fastening belt 25. Thereby, the attachment of the pulse oximeter 1 onto the living body is detected. As shown in FIG. 14A, the on-off switch 29 is turned off by disengagement of the protrusion 27 from the recess 28. Thereby, the detachment of the pulse oximeter 1 from the living body is detected. The on-off switch 29 may be arranged at an appropriate position on the recess 28.

(2) In the foregoing embodiment, the blood oxygen saturation is calculated based on the detected light amount of the light detector 6. Alternatively, a pulse rate of the subject may be additionally calculated.

(3) In the foregoing embodiment, when the blood oxygen saturation is calculated, the blood oxygen saturation data is sequentially stored in the external storage 12. Upon completion of the measurement, the ODI is calculated based on the blood oxygen saturation data stored in the external storage 12. Alternatively, a change in blood oxygen saturation calculated based on an output from the probe 3 may be monitored on a real-time basis, the number of times when the blood oxygen saturation is lowered than a predetermined threshold value may be counted as the number of sleep apneas, an elapsed time of the respective sleep apneas from start of the measurement may be stored in association with the number of sleep apneas i.e. a count value, and an ODI may be calculated based on the stored data concerning the number of sleep apneas and the measurement period upon completion of the measurement.

In the foregoing embodiment, the external storage 12 is provided in light of a need of a storage having a relatively large storage capacity in order to sequentially store the calculated blood oxygen saturation data. The above modified embodiment enables to eliminate the need of storing a large amount of data, as required in the foregoing embodiment for the following reason. Specifically, data required for calculating an ODI can be stored in the internal storage 20 of the main controller 13 in the modified embodiment by storing the data concerning the elapsed time of the respective sleep apneas from start of the measurement in association with the number of sleep apneas i.e. the count value. This eliminates provision of the external storage 12 as required in the embodiment, and to suppress cost increase and size increase of the pulse oximeter. In the modified embodiment, the internal storage 20 corresponds to the storage in the claimed invention.

(4) In the foregoing embodiment, the point of time when the data is erased from the external storage 12 is the point of time when a certain time has elapsed from the point of time when the probe 3 has been detached from the fingertip. Alternatively, a certain point of time e.g. every 12:00 p.m. (high noon) may be the point of time when the data is erased in light of a fact that, in screening a SAS, normally an overnight pulse oximetry is conducted, and a daytime pulse oximetry is hardly conducted.

(5) The foregoing embodiment discloses, as described referring to FIG. 9, the arrangement that a judgment as to whether an overnight pulse oximetry is handled as a series of measurements based on the length of the non-measurement period i.e. the measurement interruption period. Alternatively, a period during which an overnight pulse oximetry is handled as a series of measurements may be predefined as a scheduled measurement period, and measurement data that has been acquired during the scheduled measurement period after attachment of the measurement unit 3 may be handled as a series of measurement data. The scheduled measurement period may be set, using the setting input section 101.

FIG. 15 is a time chart to be used in the case where the scheduled measurement period is predefined. FIG. 15 shows an example, in which the scheduled measurement period is defined from 23:00 p.m. to 07:00 a.m. on a next day in association with actual time information. Measurement periods 1, 2, and 3 in FIG. 15 correspond to periods in the scheduled measurement period during which respective blood oxygen saturation data have been measured after attachment of the probe 3. Referring to FIG. 15, the scheduled measurement period includes two measurement interruption periods. Similarly to the arrangement shown in FIG. 9, an ODI is calculated and displayed, using the measurement data that have been acquired until the respective measurement interruptions, during the respective measurement interruption periods. The arrangement in FIG. 15 is, however, different from the arrangement in FIG. 9 in that at 07:00 a.m. when the scheduled measurement period is terminated, a period corresponding to a series of measurements is terminated, irrespective of the length of the non-measurement period after termination of the measurement period 3. In the example of FIG. 15, the ODI which is calculated based on the respective measurement data acquired in the measurement periods 1, 2, and 3, and which is displayed at 07:00 a.m. is defined as a definite value in the series of measurements. The modified embodiment restricts a measurement data acquisition period within the scheduled measurement period, which eliminates a judgment on the length of the non-measurement period, and enables to acquire ODI data by simplifying the ODI acquisition process.

In the modified embodiment, if the measurement is continued i.e. the subject is not awakened at 07:00 a.m. after the attachment of the probe 3, the measurement may be forcibly terminated. Further alternatively, a period until the probe 3 is detached after the termination of the scheduled measurement period may be included in the period corresponding to a series of measurements. Further alternatively, a certain period e.g. 8 hours from the point of time when the probe 3 is attached may be defined as the scheduled measurement period, in place of defining the scheduled measurement period in association with actual time information.

(6) In the case where the subject requires a long-term ODI measurement from several days to several weeks, it is required to accurately acquire ODI data corresponding to a required number of times of measurements i.e. required measurement days, and to submit the ODI data to a medical doctor or an equivalent expert. In view of this, the pulse oximeter may be provided with a function of counting the number of times when a series of measurements (normally, an overnight pulse oximetry) has been executed (days may be used), so that the subject can confirm a progress of the long-term ODI measurement.

The aforementioned embodiment essentially includes the invention having the following arrangements. An aspect of the invention is directed to a vital information measuring device comprising: a measuring unit for measuring certain vital information concerning a living body; a storage for storing therein a signal outputted from the measuring unit as measurement data; a vital information acquirer for acquiring a sleep apnea index based on the measurement data stored in the storage; a display section for displaying the sleep apnea index acquired by the vital information acquirer; and a device body for integrally mounting the measuring unit, the storage, the vital information acquirer, and the display section.

When the certain vital information is measured by the measuring unit, the signal outputted from the measuring unit is stored in the storage as the measurement data. Then the sleep apnea index is acquired by the vital information acquirer based on the measurement data stored in the storage, and the acquired sleep apnea index is displayed on the display section. Thus, when the measurement is completed, the sleep apnea index is acquired, and the acquired sleep apnea index is displayed on the display section. These operations/processes are executed in the device body. The integral mounting not only includes an arrangement that all the components of the device body are encased in a casing member, but also embraces an arrangement in which a part of the components of the device body is incorporated in a member other than the casing member, as far as the arrangement can be considered as a substantially integral mounting.

The above arrangement enables to realize the vital information measuring device provided with the function of acquiring and displaying the sleep apnea index in the device body. This allows the user to confirm the ODI promptly after the measurement completion, without imposing the user of the pulse oximeter to designate an operation of acquiring the ODI after the measurement completion, using a personal computer, as required in the conventional art.

Preferably, the vital information measuring device may further comprise: a mounted state detector for detecting a mounted state of the vital information measuring device onto the living body; and a measurement controller for controlling the measuring unit to start a measuring operation when the mounted state detector detects that the vital information measuring device is detachably attached to the living body, and to terminate the measuring operation when the mounted state detector detects that the vital information measuring device is detached from the living body.

In the above arrangement, when the mounted state detector detects that the vital information measuring device is detachably attached to the living body, the measurement controller controls the measuring unit to start the measuring operation. When the mounted state detector detects that the vital information measuring device is detached from the living body, the measurement controller controls the measuring unit to terminate the measuring operation. This allows the measuring unit to automatically start and terminate the measuring operation.

The above arrangement enables to realize the vital information measuring device that allows the measuring unit to automatically start and terminate the measuring operation depending on the mounted state of the vital information measuring device onto the living body. This provides enhanced operability of the vital information measuring device.

Preferably, the vital information measuring device may further comprise: a judger for judging whether a current time has reached a predetermined point of time after termination of a measuring operation of the measuring unit, wherein the vital information acquirer acquires the sleep apnea index, using the measurement data that have been acquired by the respective consecutive measuring operations of the measuring unit before and after a non-measurement period if the measuring operation of the measuring unit is resumed before the judger judges that the current time has reached the predetermined point of time.

In the above arrangement, if the measuring operation of the measuring unit is resumed before the judger judges that the current time has reached the predetermined point of time after the termination of the measuring operation, the vital information acquirer acquires the sleep apnea index, using the measuring data that have been acquired by the respective consecutive measuring operations of the measuring unit before and after the non-measurement period. With this arrangement, in the case where the measurement data that has been acquired by the measuring operation before the non-measurement period is judged to be used in acquiring the sleep apnea index, the sleep apnea index is acquired based on data including the measurement data, if the measuring operation of the measuring unit is resumed before the judger judges that the current time has reached the predetermined point of time after the termination of the measuring operation of the measuring unit. The condition that the measuring operation of the measuring unit is resumed before the judger judges that the current time has reached the predetermined point of time after the termination of the measuring operation of the measuring unit corresponds to a state that the vital information measuring device is temporarily detached for a short period inadvertently or intentionally.

According to the above arrangement, a more accurate sleep apnea index can be acquired.

Preferably, the vital information measuring device may further comprise: a data eraser for erasing the measurement data stored in the storage if the judger judges that the current time has reached the predetermined point of time.

In the above arrangement, the data eraser erases the measurement data stored in the storage if the judger judges that the current time has reached the predetermined point of time. This enables to adopt a storage having a smaller storage capacity as the storage to be mounted in the vital information measuring device, as compared with an arrangement that all the signals obtained by measuring operations of the measuring unit are stored in a storage.

According to the above arrangement, a storage with a relatively small storage capacity can be used as the storage to be mounted in the vital information measuring device. This contributes to suppression of cost increase and size increase of the vital information measuring device.

Preferably, the predetermined point of time may be a point of time when a certain time has elapsed after the termination of the measuring operation of the measuring unit, or a point of time when the current time has reached a targeted point of time.

The above arrangement enables to facilitate a judgment as to whether the measurement data that has been acquired by the measuring operation before the non-measurement period concerning the measuring operations that have been executed consecutively before and after the non-measurement period is to be used in acquiring the sleep apnea index, or the measurement data is to be erased. The above arrangement enables to easily configure a program for executing the above judgment.

Preferably, the vital information measuring device may further comprise: a scheduled measurement period setter for setting a period during which a series of measuring operations of the measuring unit are to be conducted, as a predetermined scheduled measurement period, wherein the vital information acquirer acquires the sleep apnea index, using the measurement data that have been acquired by the respective consecutive measuring operations of the measuring unit before and after a non-measurement period even if the scheduled measurement period includes the non-measurement period by restart of the measuring operation after an ongoing measurement operation has been temporarily interrupted.

In the above arrangement, even if the non-measurement period is included in the scheduled measurement period set by the scheduled measurement period setter, or the non-measurement period is partly included in the scheduled measurement period, the vital information acquirer acquires the sleep apnea index, using the measurement data that have been acquired by the measuring operations executed in the scheduled measurement period irrespective of the length of the non-measurement period.

The above arrangement enables to constrain a measurement data acquisition period within the scheduled measurement period, thereby simplifying the process of acquiring the sleep apnea index.

Preferably, the scheduled measurement period setter may set the scheduled measurement period in association with actual time information. In this arrangement, the scheduled measurement period is set based on a specific point of time, considering, for instance, a scheduled sleep period of the living body i.e. a subject.

According to the above arrangement, since the scheduled measurement period is set based on the specific point of time, operability of the user is enhanced.

Preferably, in the case where a predetermined scheduled measurement period includes a non-measurement period, a first measurement period, and a second measurement period, with the non-measurement period being in between the first measurement period and the second measurement period, by restart of the measuring operation of the measuring unit after an ongoing measuring operation has been temporarily interrupted, the measurement data that has been acquired in the first measurement period, the measurement data that has been acquired in the second measurement period, and the measurement data that has been acquired throughout the first measurement period and the second measurement period may be individually storable into the storage.

In the above arrangement, in the case where the scheduled measurement period includes the non-measurement period, the first measurement period, and the second measurement period, with the non-measurement period being in between the first measurement period and the second measurement period, the measurement data that has been acquired in the first measurement period, the measurement data that has been acquired in the second measurement period, and the sum of the measurement data that have been acquired throughout the first measurement period and the second measurement period are individually stored into the storage. This arrangement enables to acquire the sleep apnea index in the first measurement period, the sleep apnea index in the second measurement period, and the sleep apnea index in the series of measurement periods, with the non-measurement period being in between the first measurement period and the second measurement period.

According to the above arrangement, the sleep apnea indexes can be assessed individually with respect to the first measurement period, the second measurement period, and the series of measurement periods, with the non-measurement period being in between the first measurement period and the second measurement period, which enables to expand an assessment range.

Preferably, the vital information measuring device may further comprise: a data eraser for erasing the measurement data stored in the storage, after the sleep apnea index is acquired by the vital information acquirer and the acquired sleep apnea index is stored in the storage.

In the above arrangement, the data eraser erases the raw measurement data, after the sleep apnea index is acquired and the acquired sleep apnea index is stored in the storage. This allows for exclusively storing the sleep apnea index obtained as a result of computation into the storage.

According to the above arrangement, since the storage exclusively stores the sleep apnea index obtained as the result of computation, the data capacity of the storage can be saved.

Preferably, the vital information measuring device may further comprise a setting information setter for accepting setting information relating to operations of respective parts of the vital information measuring device to perform a setting relating to the setting information with respect to the respective parts of the vital information measuring device, wherein the setting information setter classifies an area where the setting information is accepted for performing the setting at least into a first setting area where an access authorization process is required, and a second setting area where the access authorization process is not required in accepting the setting information.

In the above arrangement, in the case where various setting information is set in the vital information measuring device, the setting information setter classifies the setting area into the first setting area where the access authorization process is required, and the second setting area where the access authorization process is not required in accepting the setting information. This arrangement enables to properly use the vital information measuring device by setting the setting information of a kind in which an unauthorized change in setting information may obstruct the measurement in the first setting area, and by setting the setting information of a kind in which an arbitrarily change is recommended depending on a measurement environment in the second setting area.

According to the above arrangement, the setting area is classified into two categories i.e. the first setting area where the access authorization process is required in performing the setting with respect to the vital information measuring device, and the second setting area where the access authorization process is not required. With this arrangement, the setting information that should be set depending on a diagnosis purpose of a person in charge of diagnosis e.g. a medical doctor, and accordingly should not be changed by the subject is defined in the first setting area, and the setting information that is recommended to be arbitrarily set by the subject depending on a measurement environment is defined in the second setting area. This ensures proper use of the vital information measuring device.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A vital information measuring device comprising:
a measuring unit for measuring certain vital information concerning a living body on a predetermined cycle;
a storage for storing therein a plurality of signals outputted from the measuring unit as measurement data;
a vital information acquirer for acquiring a sleep apnea index based on a plurality of the measurement data measured in consecutive measuring periods stored in the storage;
a display section for displaying the sleep apnea index acquired by the vital information acquirer; and
a device body for integrally mounting the measuring unit, the storage, the vital information acquirer, and the display section, wherein
the vital information acquirer acquires the sleep apnea index based on the measurement data measured in respective consecutive measuring periods before and after a non-measurement period when the measuring period is temporarily interrupted.

2. The vital information measuring device according to claim 1, further comprising:
a mounted state detector for detecting a mounted state of the vital information measuring device onto the living body; and
a measurement controller for controlling the measuring unit to start a measuring operation when the mounted state detector detects that the vital information measuring device is detachably attached to the living body, and to terminate the measuring operation when the mounted state detector detects that the vital information measuring device is detached from the living body.

3. The vital information measuring device according to claim 1, further comprising:
a judger for judging whether a current time has reached a predetermined point of time after termination of a measuring operation of the measuring unit, wherein
the vital information acquirer acquires the sleep apnea index, using the measurement data that have been acquired by the respective consecutive measuring operations of the measuring unit before and after a non-measurement period if the measuring operation of the measuring unit is resumed before the judger judges that the current time has reached the predetermined point of time.

4. The vital information measuring device according to claim 3, further comprising:
a data eraser for erasing the measurement data stored in the storage if the judger judges that the current time has reached the predetermined point of time.

5. The vital information measuring device according to claim 3, wherein
the predetermined point of time is a point of time when a certain time has elapsed after the termination of the measuring operation of the measuring unit, or a point of time when the current time has reached a targeted point of time.

6. The vital information measuring device according to claim 3, wherein
in the case where a predetermined scheduled measurement period includes a non-measurement period, a first measurement period, and a second measurement period, with the non-measurement period being in between the first measurement period and the second measurement period, by restart of the measuring operation of the measuring unit after an ongoing measuring operation has been temporarily interrupted, the measurement data that has been acquired in the first measurement period, the measurement data that has been acquired in the second measurement period, and the measurement data that have been acquired throughout the first measurement period and the second measurement period are individually storable into the storage.

7. The vital information measuring device according to claim 1, further comprising:
a scheduled measurement period setter for setting a period during which a series of measuring operations of the measuring unit are to be conducted, as a predetermined scheduled measurement period, wherein the vital information acquirer acquires the sleep apnea index, using the measurement data that have been acquired by the respective consecutive measuring operations of the measuring unit before and after a non-measurement period even if the scheduled measurement period includes the non-measurement period by restart of the measuring operation after an ongoing measurement operation has been temporarily interrupted.

8. The vital information measuring device according to claim 7, wherein the scheduled measurement period setter sets the scheduled measurement period in association with actual time information.

9. The vital information measuring device according to claim 7, wherein in the case where the predetermined scheduled measurement period includes the non-measurement period, a first measurement period, and a second measurement period, with the non-measurement period being in between the first measurement period and the second measurement period, by restart of the measuring operation of the measuring unit after the ongoing measuring operation has been temporarily interrupted, the measurement data that has been acquired in the first measurement period, the measurement data that has been acquired in the second measurement period, and the measurement data that have been acquired throughout the first measurement period and the second measurement period are individually storable into the storage.

10. The vital information measuring device according to claim 1, further comprising:

a data eraser for erasing the measurement data stored in the storage, after the sleep apnea index is acquired by the vital information acquirer and the acquired sleep apnea index is stored in the storage.

11. The vital information measuring device according to claim 1, further comprising a setting information setter for accepting setting information relating to operations of respective parts of the vital information measuring device to perform a setting relating to the setting information with respect to the respective parts of the vital information measuring device, wherein the setting information setter classifies an area where the setting information is accepted for performing the setting at least into a first setting area where an access authorization process is required, and a second setting area where the access authorization process is not required in accepting the setting information.

12. The vital information measuring device according to claim 1, wherein the non-measurement period includes a period when the vital information measuring device is detached from the living body.

13. The vital information measuring device according to claim 1, wherein the non-measurement period includes a period of wakefulness.

14. The vital information measuring device according to claim 1, wherein the non-measurement period includes a period of motion.

* * * * *